(12) United States Patent
Im

(10) Patent No.: US 12,114,842 B2
(45) Date of Patent: Oct. 15, 2024

(54) EXFOLIATIVE CELL COLLECTION DEVICE FOR UTERUS EXAMINATION

(71) Applicant: BIODYNE CO., LTD., Gyeonggi-do (KR)

(72) Inventor: Wook Bin Im, Seongnam-si (KR)

(73) Assignee: BIODYNE CO., LTD., Seoul (KR)

( * ) Notice: Subject to any disclaimer, the term of this patent is extended or adjusted under 35 U.S.C. 154(b) by 715 days.

(21) Appl. No.: 17/292,698

(22) PCT Filed: Jan. 1, 2020

(86) PCT No.: PCT/KR2020/000003
§ 371 (c)(1),
(2) Date: May 10, 2021

(87) PCT Pub. No.: WO2020/171371
PCT Pub. Date: Aug. 27, 2020

(65) Prior Publication Data
US 2021/0393244 A1 Dec. 23, 2021

(30) Foreign Application Priority Data
Feb. 21, 2019 (KR) .................. 10-2019-0020610

(51) Int. Cl.
*A61B 10/02* (2006.01)
(52) U.S. Cl.
CPC .. *A61B 10/0291* (2013.01); *A61B 2010/0208* (2013.01); *A61B 2010/0216* (2013.01)

(58) Field of Classification Search
CPC ............... A61B 10/0291; A61B 10/02; A61B 2010/0208; A61B 2010/0216; A61B 2010/0074
See application file for complete search history.

(56) References Cited

U.S. PATENT DOCUMENTS

| | | | |
|---|---|---|---|
| 2,847,990 A * | 8/1958 | Ayre | ...................... A61B 10/04 600/569 |
| 6,402,700 B1 * | 6/2002 | Richards | ............ A61B 17/3431 600/562 |

FOREIGN PATENT DOCUMENTS

| | | |
|---|---|---|
| KR | 10-2005-009911 A | 10/2005 |
| KR | 10-2006-0103768 A | 10/2006 |
| KR | 10-2015-0087230 A | 7/2015 |

(Continued)

*Primary Examiner* — Alex M Valvis
*Assistant Examiner* — Nidhi N Patel
(74) *Attorney, Agent, or Firm* — PARK LAW FIRM

(57) ABSTRACT

The present invention is a technology relating to a device for collecting exfoliative cells at cervix and its surrounding area for uterus examination. The present invention relates to a technology for providing good usability in collecting exfoliative cells at cervix and its surrounding area corresponding to their current state by dividing a brush for contacting the cervix and its surrounding area into an insertion brush and a tension brush and then letting the shape of the tension brush be gradually changing by user operation. The present invention has an advantage in that the separative rod may be robustly attached to the movable rod until user operation is applied to the push separation member even when the movable rod is sufficiently moved forward since the first latching hook of the movable rod and the second latching hook of the separative rod are hook-latched each other.

3 Claims, 11 Drawing Sheets

(56) References Cited

FOREIGN PATENT DOCUMENTS

| KR | 10-2015-0116997 A | 10/2015 |
| KR | 10-2017-0138064 A | 12/2017 |

* cited by examiner (a)          (b)

EXFOLIATIVE CELL COLLECTION DEVICE FOR UTERUS EXAMINATION

FIELD OF THE INVENTION

The present invention is a technology relating to a device for collecting exfoliative cells at cervix and its surrounding area for uterus examination.

More specifically, the present invention relates to a technology for providing good usability in collecting exfoliative cells at cervix and its surrounding area corresponding to their current state by dividing a brush for contacting the cervix and its surrounding area into an insertion brush and a tension brush and then letting the shape of the tension brush be gradually changing by user operation.

BACKGROUND ART

In general, it is proposed to collect and inspect exfoliative cells at cervix and its surrounding area in order to screen the health of uterus.

In the future, in collecting exfoliative cells at cervix and its surrounding area, a user may collect exfoliative cells at her cervix and its surrounding area for herself with a collection brush (e.g., a disposable brush), and then may send the collected matters and a part of the collection brush (e.g., a brush portion) to which the collected matters are attached, for example, in a vial, to an inspection institution (e.g., a hospital) for inspection.

Since the collection brush is used by a user for himself, the brush mush provide good usability and safety.

FIG. 1 is a simplified illustration of the periphery of uterus and cervix. Referring to FIG. 1, the cervix of relatively narrow passage is located at boundary portion from vagina to the inside of uterus, the internal os is located in the cervix toward the inside of uterus, and the ectcervix is located in the cervix toward the vagina. In addition, the external os, the endocervix, and the endometrial canal is sequentially located in the cervix from the vagina to the inside of uterus.

The names in FIG. 1 are used for specifying each position of cervix and its surrounding area in order to illustrate that the collection brush can collect exfoliative cells for uterus examination with moving its position in the cervix and its surrounding area. The position for each of names in FIG. 1 may be medically incorrect.

Referring to FIG. 1, the shape of the cervix and its surrounding area may vary with biological age and health condition. For example, young women have wider ectocervix portion as well as wider and shorter cervix portion from vagina to uterus than older women.

Therefore, in collecting exfoliative cells at cervix and its surrounding area, it is needed to provide the collection brushes in various specifications in shape.

In this circumstance, a user shall consume several collection brushes in order to know the appropriate shape of collection brush which is suitable for her cervix and its surrounding area for herself In order to overcome this disadvantage, the shape of the brush portion may be adjusted corresponding to, for example, the current state of her cervix and its surrounding area (e.g., age, health condition), so that exfoliative cells may be smoothly collected at cervix and its surrounding area in various situations (e.g., age, health condition).

In addition, in order to collect exfoliative cells at cervix and its surrounding area, the collection brush shall be inserted into the vagina. It would be dangerous if a part of collection brush (e.g., the brush portion) is separated while the collection brush is inserted into the vagina. Therefore, a safety apparatus is required for preventing the brush portion from being released when the user is not intended to.

Accordingly, it is necessary to adjust the shape of collection brush by user operations as well as to adopt a safety apparatus for preventing a part of the collection brush from being released in the vagina when the user is not intended to.

DISCLOSURE OF INVENTION

Technical Problem

The present invention has been proposed in view of the above-mentioned features. It is an object of the present invention to provide an exfoliative cell collection device for uterus examination, which may provide good usability corresponding to current state of cervix and its surrounding area (e.g., shape of the cervical part) by dividing a brush for contacting the cervix and its surrounding area into an insertion brush and a tension brush and then letting the shape of the tension brush be gradually changing by user operation.

Further, it is an object of the present invention to provide an exfoliative cell collection device for uterus examination, which may collect a sufficient amount of specimen cells by increasing the contact area corresponding to the state of cervix and its surrounding area.

Further, it is an object of the present invention to provide an exfoliative cell collection device for uterus examination, which may prevent a part of the exfoliative cell collection device from being released while an insertion brush and a tension brush are inserted into vagina when the user is not intended to.

Technical Solution

In order to achieve the above object, the present invention is an exfoliative cell collection device for uterus examination for collecting exfoliative cells at cervix and its surrounding area, comprising: an insertion brush (111) being inserted into a cervix; a separative rod (120) being connected to a rear end portion of the insertion brush, wherein the separative rod (120) is longitudinally stroked forward or backward along the insertion brush; an outer cylinder member (130) having a hollow cylindrical shape through which the rear end portion of the separative rod may go in and out, wherein the outer cylinder member (130) guides the forward and backward strokes of the separative rod; a holder member (112) being detachably connected to a front end portion of the outer cylinder member with surrounding the front end portion of the outer cylinder member; a plurality of tension brush (113) being mounted along the rim of the holder member, wherein one end of each tension brush is connected to the holder member and the other end of each tension brush is connected to the rear end portion of the insertion brush so as to be compatible with the shape of inside and outside of the cervix, wherein each tension brush provides gradual longitudinal extension by gradual unfolding in association with the forward stroke of the separative rod, and wherein each tension brush provides gradual lateral extension by gradual folding in association with the backward stroke of the separative rod; a movable rod (140) being detachably connected to the rear end portion of the separative rod while being inserted into the inner side of the outer cylinder member, wherein the movable rod (140) strokes the separative rod forward or backward when the movable rod (140) is longitudinally stroked forward or backward along the outer cylinder member; a pressing block (141) being connected to the rear end portion of the movable rod, wherein the pressing block (141) strokes the movable rod forward or backward when the pressing block (141) goes in and out of the outer cylinder member by user operation in the rear end portion of the outer cylinder member; and a tension pressing member (150) being longitudinally connected to the side of the movable rod, wherein the tension pressing member (150) holds position of the movable rod by pressing the inner wall of the outer cylinder member so as to block a natural movement of the movable rod forward or backward.

In the present invention, the outer cylinder member (130) may include: a plurality of latching holes (131) being longitudinally formed along the outer cylinder member adjacent to the tension pressing member, wherein the latching holes (131) penetrate the inside and outside of the outer cylinder member; and a latching slot (132) being formed in a slot shape longitudinally extending along the outer cylinder member, wherein the latching slot (132) is positioned on the holder member than the latching holes are. Further, the tension pressing member (150) includes: a plurality of position adjusting protrusions (151) protruding to contact the inner wall of the outer cylinder member along the longitudinal direction of the tension pressing member, wherein the position adjusting protrusions (151) are positioned corresponding to the plurality of latching holes, wherein the position adjusting protrusions (151) are individually inserted into the plurality of latching holes by the elastic force of the tension pressing member, and wherein the position of the latching holes into which the position adjusting protrusions (151) are inserted changes by the forward or backward stroke of the movable rod; and a pressing protrusion (152) protruding along the longitudinal direction of the tension pressing member, wherein the pressing protrusion (152) is positioned on the holder member than the position adjusting protrusions are, wherein the pressing protrusion (152) is inserted into the latching slot by the elastic force of the tension pressing member, wherein the pressing protrusion (152) protrudes more than the position adjusting protrusions so that a user's push operation while the pressing protrusion (152) is inserted into the latching slot enables the position change between the latching holes and the position adjusting protrusions. The present invention may further comprise: a backward pressing member (160) being disposed between the rod stopper (171) and the outer cylinder stopper (172) in the inner side of the outer cylinder member, wherein the backward pressing member (160) has a spring having one end contacting the rod stopper (171) and the other end contacting the outer cylinder stopper (172), and wherein the backward pressing member (160) provides the movable rod (140) with backward elastic force so that the movable rod (140) continuously has the force of backward moving as the spring presses the rod stopper (171) with respect to on the outer cylinder stopper (172).

The present invention may further comprise: a rod stopper (171) protruding from the movable rod; and an outer cylinder stopper (172) protruding inward from the inner wall of the outer cylinder member at a relatively forward position than the rod stopper. As a backward pressing member presses the rod stopper based on the outer cylinder stopper, the movable rod continuously has the force of backward moving.

Further, the movable rod (140) may include: a first latching hook (142) having a bended front end portion for providing a hook attachment and detachment. Further, the separative rod (120) may include: a second latching hook (121) having a bended rear end portion for providing a hook attachment and detachment with the first latching hook (142); and a guide rib (122) protruding around the rim of body portion thereof adjacent to the second latching hook, wherein the guide rib (122) contacts the inner wall of the outer cylinder member by the protrusion, and wherein the guide rib (122) guides the forward and backward strokes of the separative rod.

Further, the present invention may further comprise: a push-releasing member (180) pushing the front end portion of the movable rod from the inner wall of the outer cylinder member while being mounted on the outer cylinder member.

Further, the present invention may further comprise: a tension hook member (190) being formed at the front end portion of the outer cylinder member, wherein the front end portion of the outer cylinder member is connected to the holder member, wherein the tension hook member (190) fits inside of the holder member in a hook shape by an elastic force when the tension hook member (190) slides into the holder member, and wherein the tension hook member (190) is released from the holder member by a series of forward strokes of the separative rod through the longitudinal extension of the tension brush by the forward stroke of the separative rod.

Advantageous Effects

The present invention has an advantage in that the shape of the tension brush may be adjusted stepwise by user operations in response to the current state of cervix and its surrounding area by including latching holes and latching slots of the outer cylinder member as well as position adjusting protrusions and a pressing protrusion of the tension pressing member.

Further, the present invention has an advantage in that a sufficient amount of exfoliative cells may be effectively collected for uterus examination since the shape of the tension brush may be adjusted stepwise in response to the current state of cervix and its surrounding area so as to sufficiently widen the contact area with the cervix and its surrounding area.

Further, the present invention has an advantage in that user's pain may be minimized since a sufficient amount of exfoliative cells may be collected only by rotating the tension brush by small angle (e.g., 90 degrees) in collecting exfoliative cells for uterus examination as the shape of the tension brush may be adjusted by longitudinal extension as well as lateral extension.

Further, the present invention has an advantage in that users may simultaneously collect exfoliative cells at cervix as well as inner area of uterus by one operation since the insertion brush and the tension brush are provided together.

Further, the present invention has an advantage in that the separative rod may be robustly attached to the movable rod until user operation is applied to the push separation member even when the movable rod is sufficiently moved forward since the first latching hook of the movable rod and the second latching hook of the separative rod are hook-latched each other.

Further, the present invention has an advantage in that the contamination of the collected exfoliative cells may be prevented since the separative rod is released from the movable rod by the operation to the push-releasing member.

EMBODIMENT FOR CARRYING OUT THE INVENTION

Hereinafter, the present invention will be described in detail with reference to the drawings.

Figure 2:
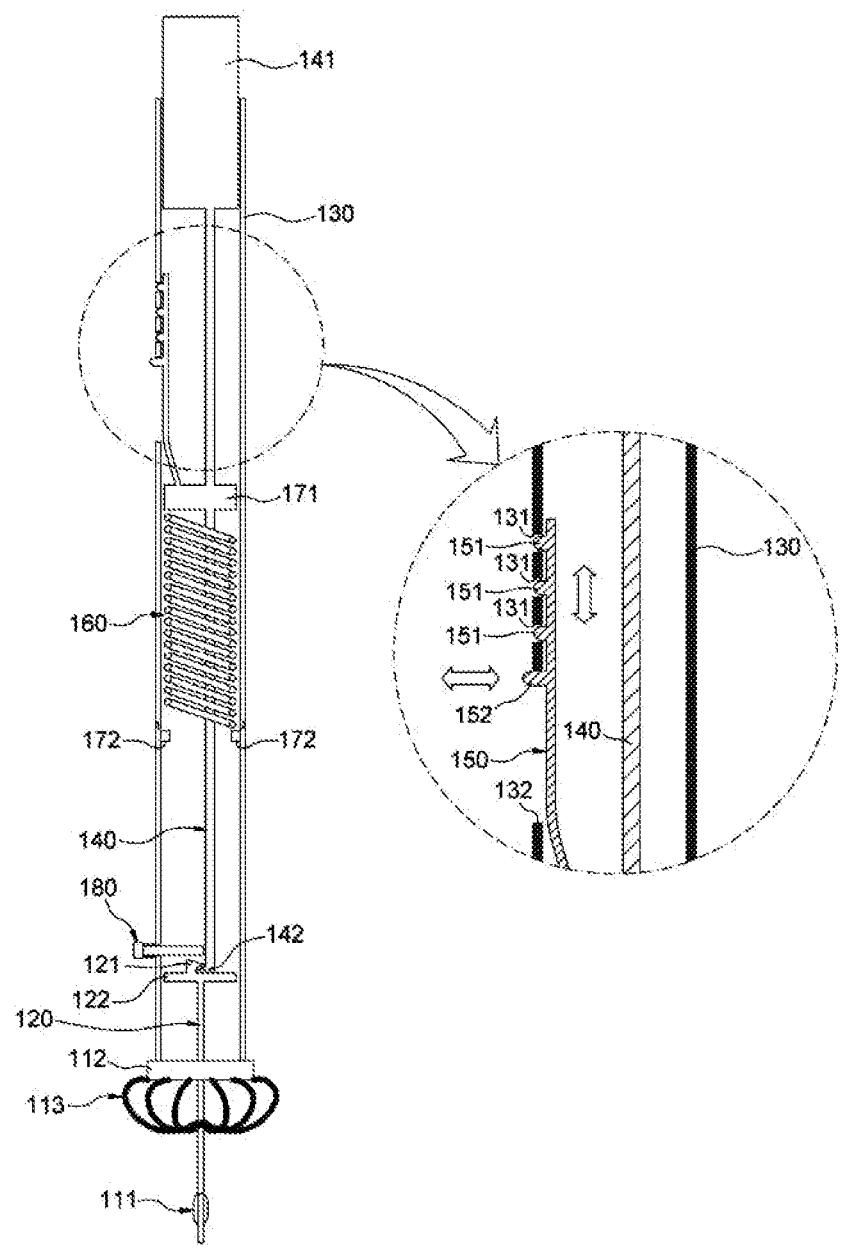
FIG. 2 is an exemplary view and its partial enlarged view in which the movable rod has moved backwards in the present invention.
Figure 3:
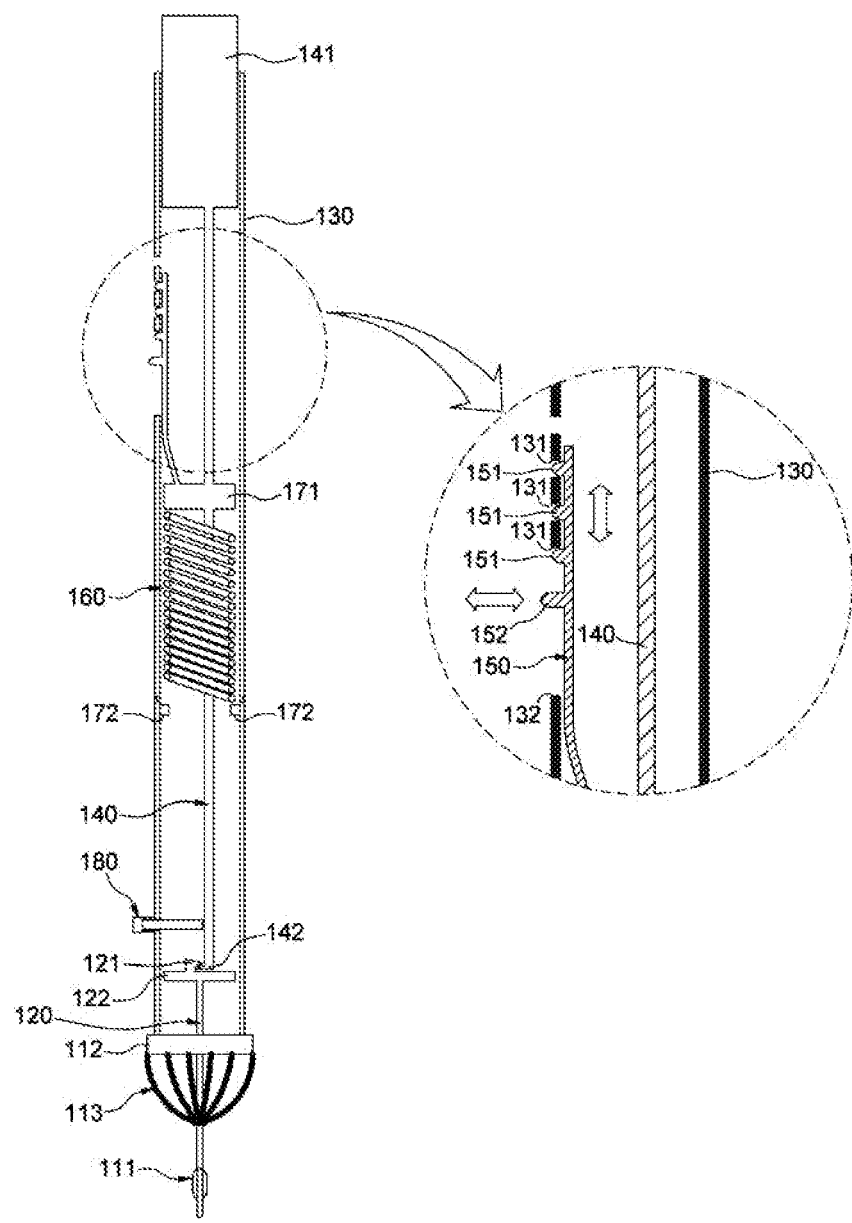
FIG. 3 is a view showing FIG. 2 in which the movable rod has moved one step forward.
Figure 4:
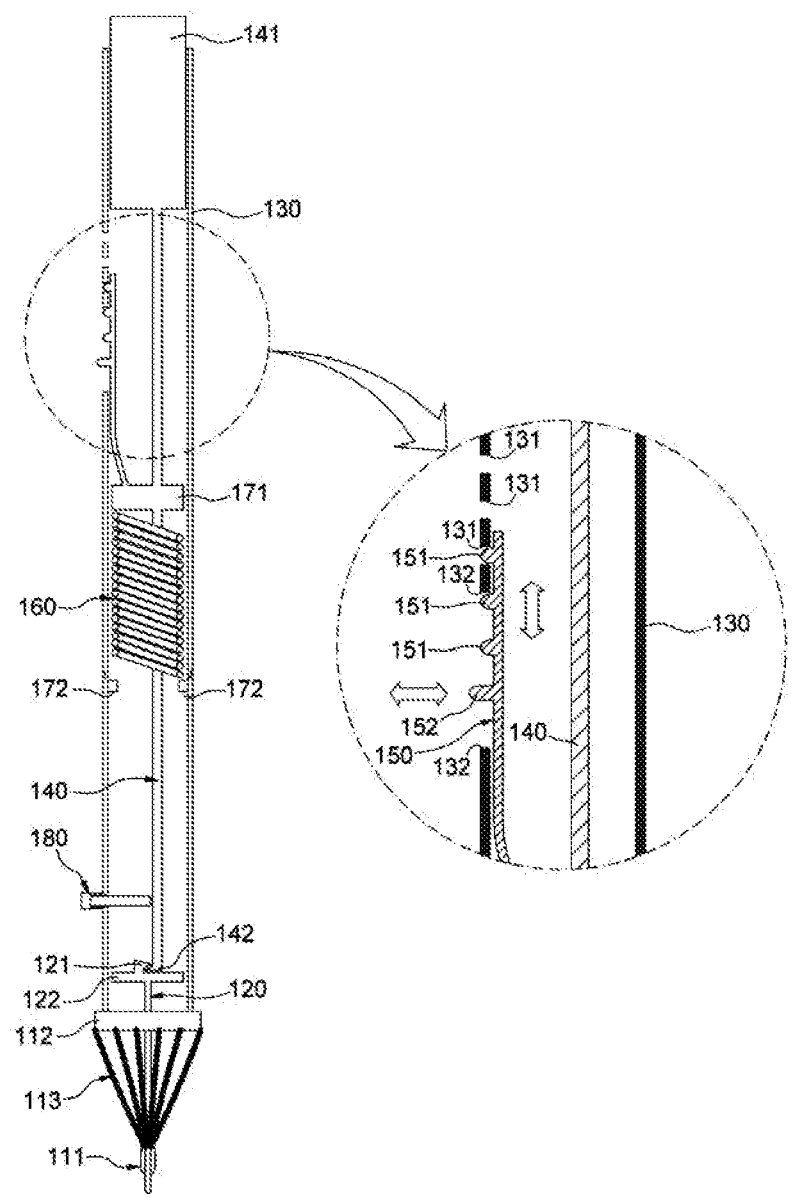
FIG. 4 is a view showing FIG. 3 in which the movable rod has moved one step forward.
Figure 5:
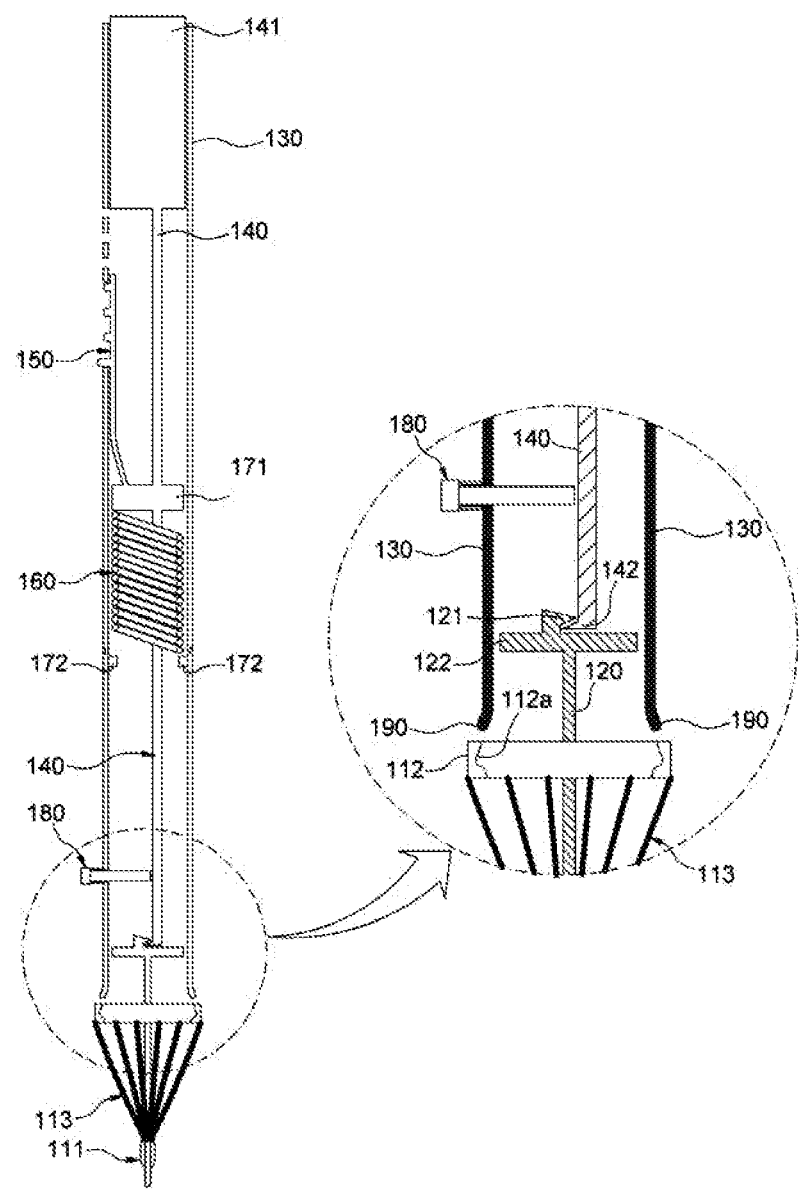
FIG. 5 is a view showing FIG. 4 in which the movable rod has moved forward so as to let the holder member be released from the tension hook member and the second latching hook is latched to the first latching hook so as to let the separative rod be connected to the movable rod.

FIG. 2 is an exemplary view and its partial enlarged view in which the movable rod has moved backwards in the present invention. FIG. 3 is a view showing FIG. 2 in which the movable rod has moved one step forward. FIG. 4 is a view showing FIG. 3 in which the movable rod has moved one step forward. FIG. 5 is a view showing FIG. 4 in which the movable rod has moved forward so as to let the holder member be released from the tension hook member and the second latching hook is latched to the first latching hook so as to let the separative rod be connected to the movable rod.

Referring to FIGS. 2 to 5, the present invention relates to a device for collecting exfoliative cells at endometriosis and its surroundings for uterus examination, and may comprise a insertion brush (111), a separative rod (120), an outer cylinder member (130), a holder member (112), a tension brush (113), a movable rod (140), a pressing block (141), a tension pressing member (150), a backward pressing member (160), a rod stopper (171), an outer cylinder stopper (172), a push-releasing member (180), and a tension hook member (190).

The insertion brush (111) is a part to be inserted into a cervix, and may preferably be formed as a sharp rod as shown in FIGS. 2 to 5.

As shown in FIGS. 2 to 5, the separative rod (120) has a front end portion and a rear end portion, in which the front end portion is connected to the rear end portion of the insertion brush (111) and the rear end portion is connected to the movable rod (140). The separative rod (120) is longitudinally stroked forward or backward along the insertion brush (111) in response to a forward or backward stroke of the movable rod (140).

As shown in FIGS. 2 to 5, the outer cylinder member (130) has a hollow cylindrical shape so that the rear end portion of the separative rod (120) may go in and out through the hollow cylindrical shape. The outer cylinder member (130) may guide the forward and backward strokes of the separative rod (120).

As shown in FIGS. 2 to 5, the holder member (112) has a shape of a ring so that is detachably connected to a front end portion of the outer cylinder member (130) with surrounding the front end portion of the outer cylinder member (130).

As shown in FIGS. 2 to 5, a plurality of tension brush (113) is mounted along the rim of the holder member (112). In order to be compatible with the shape of inside and outside of the cervix, each tension brush (113) has one end being connected to the holder member (112) and the other end being connected to the rear end portion of the insertion brush (111).

When the separative rod (120) is stroked forward with reference to the holder member (112) as shown from FIGS. 2 to 4, each of the tension brushes (113) gradually unfolds in association with the forward stroke of the separative rod (120) so as to provide a gradual longitudinal extension.

When the separative rod (120) is stroked backward with reference to the holder member (112) as shown from FIGS. 4 to 2, each of the tension brushes (113) gradually folds in association with the backward stroke so as to provide a gradual lateral extension.

When the tension brushes (113) are laterally extended as shown in FIG. 2, the tension brushes (113) have a structure suitable for collecting exfoliative cells at the surroundings of entrance of cervix.

When the tension brushes (113) are longitudinally extended as shown in FIG. 4, the tension brushes (113) have a structure suitable for collecting exfoliative cells at the inner entrance of cervix because the front end portion of the tension brushes (113) can enter the inside of the cervix.

As shown in FIGS. 2 to 5, the movable rod (140) is detachably connected to the rear end portion of the separative rod (120) while being inserted into the inner side of the outer cylinder member (130). When the movable rod (140) is longitudinally stroked forward or backward along the outer cylinder member (130) by a user operation, the movable rod (140) strokes the separative rod (120) forward or backward.

As shown in FIGS. 2 to 5, the pressing block (141) is connected to the rear end portion of the movable rod (140). The pressing block (141) strokes the movable rod (140) forward or backward when the pressing block (141) goes in and out of the outer cylinder member (130) by user's push operation in the rear end portion of the outer cylinder member (130).

As shown in FIGS. 2 to 5, the tension pressing member (150) is longitudinally connected to the side of the movable rod (140). The tension pressing member (150) holds position of the movable rod (140) by pressing the inner wall of the outer cylinder member (130) so as to block a natural movement of the movable rod (140) forward or backward.

As shown in FIGS. 2 to 5, the backward pressing member (160) may comprise a spring. The backward pressing member (160) is connected to and surrounds the movable rod (140) in the inner side of the outer cylinder member (130). The backward pressing member (160) provides the movable rod (140) with backward elastic force so that the movable rod (140) continuously has the force of backward moving.

In order that the tension pressing member (150) may hold position of the movable rod (140) while longitudinally moving along the outer cylinder member (130) by the elastic force of the backward pressing member (160), the outer cylinder member (130) may preferably include latching holes (131) and a latching slot (132) and the tension pressing member (150) may preferably include a position adjusting protrusion (151) and a pressing protrusion (152).

First, as shown in FIGS. 2 to 4, the latching holes (131) may comprise a plurality of holes. The holes are longitudinally formed along the outer cylinder member (130) adjacent to the tension pressing member (150), and penetrate the inside and outside of the outer cylinder member (130).

As shown in FIGS. 2 to 4, the latching slot (132) may be formed in a slot shape which is longitudinally extending along the outer cylinder member (130), wherein the latching slot (132) is positioned on the holder member (112) than the latching holes (131) are.

In addition, as shown in FIGS. 2 to 4, the position adjusting protrusions (151) are formed to protrude to contact the inner wall of the outer cylinder member (130) along the longitudinal direction of the tension pressing member (150). The positions of the position adjusting protrusions (151) are corresponding to the plurality of latching holes (131).

As shown in FIGS. 2 to 4, the plurality of position adjusting protrusions (151) is provided. The position adjusting protrusions (151) are individually inserted into the plurality of latching holes (131) by the elastic force of the tension pressing member. A forward or backward stroke of the movable rod can change the position of the latching holes (131) into which the position adjusting protrusions (151) are inserted.

For example, the position of the latching holes (131) into which the position adjusting protrusions (151) are inserted may change from FIGS. 2 to 4 or alternatively from FIGS. 4 to 2.

As shown in FIGS. 2 to 4, the pressing protrusion (152) is formed to protrude along the longitudinal direction of the tension pressing member (150). The pressing protrusion (152) is positioned on the holder member (112) than the position adjusting protrusions (151) are.

As shown in FIGS. 2 to 4, the pressing protrusion (152) is inserted into the latching slot (132) by the elastic force of the tension pressing member (150). The pressing protrusion (152) protrudes more than the position adjusting protrusions (151). Therefore, when a user's push operation is applied on the pressing protrusion (152) while the pressing protrusion (152) is inserted into the latching slot (132), the position change between the latching holes (131) and the position adjusting protrusions (151) may be enabled.

As shown in FIGS. 2 to 5, the rod stopper (171) protrudes from the outer wall of the movable rod (140) corresponding to the rear end portion of the backward pressing member (160). The rod stopper (171) blocks a backward movement to the movable rod (140) of the backward pressing member (160).

As shown in FIGS. 2 to 5, the rod stopper (171) is formed such that the edge thereof contacts the inner wall of the outer cylinder member (130). Therefore, when the movable rod (140) is stroked forward or backward in the outer cylinder member (130), the movable rod (140) may move forward and backward without lateral shaking.

The outer cylinder stopper (172) protrudes inward from the inner wall of the outer cylinder member (130) in which the movable rod (140) is positioned. The outer cylinder stopper (172) corresponds the front end portion of the backward pressing member (160), thereby blocking a forward movement of the backward pressing member (160) with respect to the outer cylinder member (130).

Since the backward pressing member (160) presses the rod stopper (171) with respect to the outer cylinder stopper (172) due to the rod stopper (171) and the outer cylinder stopper (172), the movable rod (140) may have a backward elastic force continuously.

Meanwhile, referring to FIGS. 2 to 5, the movable rod (140) may include a first latching hook (142), and the separative rod (120) may include a second latching hook (121) and a guide rib (122).

As shown in FIGS. 2 to 5, the first latching hook (142) may have a laterally bended front end portion by which the first latching hook (142) may provide a hook attachment and detachment with the separative rod (120).

As shown in FIGS. 2 to 5, the second latching hook (121) may have a laterally bended rear end portion by which the second latching hook (121) may provide a hook attachment and detachment with the first latching hook (142).

As shown in FIGS. 2 to 5, the guide rib (122) protrudes around the rim of body portion thereof adjacent to the second latching hook (121) so that the guide rib (122) contacts the inner wall of the outer cylinder member (130) by the protrusion, thereby guiding the forward and backward strokes of the separative rod (120).

That is, as shown in FIGS. 2 to 5, the guide rib (122) is formed such that the edge thereof contacts the inner wall of the outer cylinder member (130). Therefore, when the separative rod (120) is stroked forward or backward in the outer cylinder member (130), the separative rod (120) may move forward and backward without lateral shaking.

Preferably, as shown in FIGS. 2 to 5, the push-releasing member (180) is mounted on the outer cylinder member to be adjacent to the first latching hook (142) in the maximum forward stroke of the movable rod (140).

The push-releasing member (180) pushes the front end portion of the movable rod (140) from the inner wall of the outer cylinder member (130) in response to a user's push operation so as to let the first latching hook (142) be released from the second latching hook (121).

Preferably, as shown in FIG. 5, the tension hook member (190) may be formed at the front end portion of the outer cylinder member (130) in which the outer cylinder member (130) is connected to the holder member (112).

As shown in FIGS. 2 to 4, the tension hook member (190) fits inside of the holder member (112) in a hook shape by an elastic force when the tension hook member (190) slides into the holder member (112). When a series of forward strokes of the separative rod (120) are applied, through the longitudinal extension of the tension brush (113) by the forward stroke of the separative rod (120), the tension hook member (190) may be released from the holder member (112) as shown in FIG. 5.

Alternatively, in view of the packaging for sale of the exfoliative cell collection device of the present invention, the tension brush (113) may be disposed to provide a longitudinal extension as shown in FIG. 4.

When a user is going to use the exfoliative cell collection device of the present invention, she first pushes the pressing protrusion (152) so that the tension pressing member (150) in the outer cylinder member (130) is disposed as shown in FIG. 2 by the elastic force of the backward pressing member (160) and that the tension brush (113) has the form as shown in FIG. 2.

Further, the user sequentially presses the pressing block (141) from FIG. 2 to FIG. 4. with gripping the outer cylinder member (130) so that the shape of the tension brush (113) may be adjusted corresponding to the current state of her cervix and its surrounding area.

Figure 6:
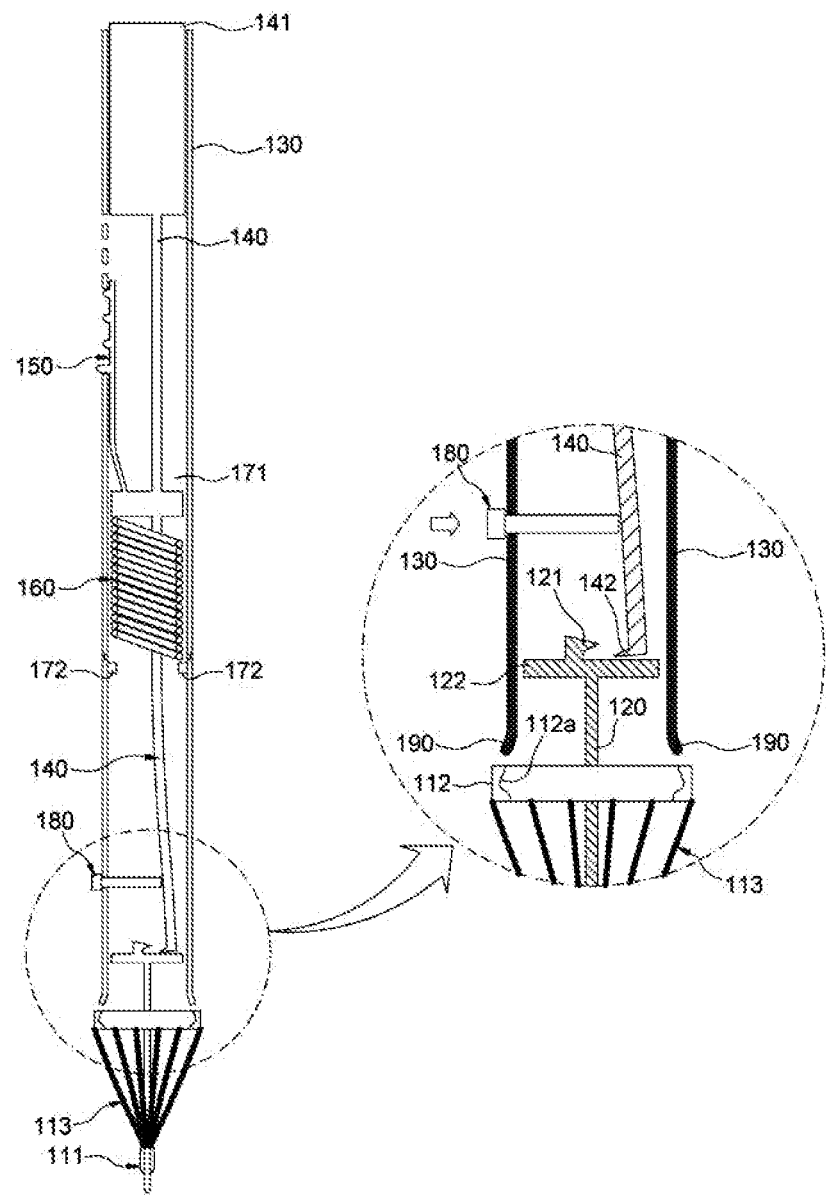
FIG. 6 is a view showing FIG. 5 in which the second latching hook is released from the first latching hook by operating the push-release member.
Figure 7:
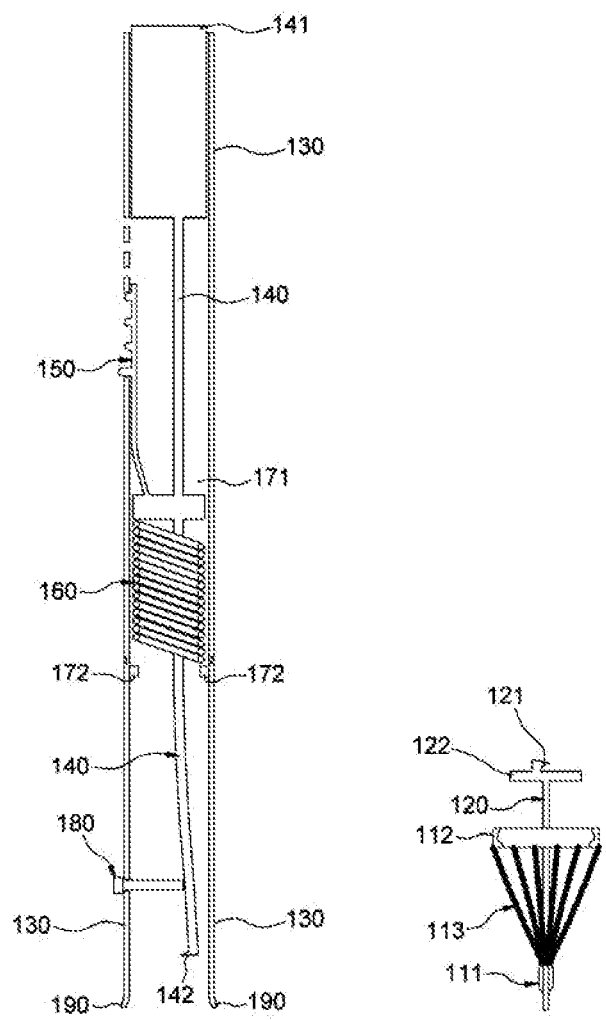
FIG. 7 is a view showing FIG. 6 in which the holder member and the separative rod are completely released from the outer cylinder member.

FIG. 6 is a view showing FIG. 5 in which the second latching hook is released from the first latching hook by operating the push-release member. FIG. 7 is a view showing FIG. 6 in which the holder member and the separative rod are completely released from the outer cylinder member.

First, as shown in FIG. 5, the tension hook member (190) is released from the holder member (112) by a series of forward strokes of the separative rod (120) through the longitudinal extension of the tension brush (113) by the forward stroke of the separative rod (120). Since the first latching hook (142) and the second latching hook (121) are hook-latched each other in the outer cylinder member (130), the separative rod (120) is still latched to the front end portion of the movable rod (140).

At this time, as shown in FIG. 6, when the user pushes the push-releasing member (180), the first latching hook (142) which is latched to the second latching hook (121) moves in the lateral direction so that the separative rod (120) may be released from the movable rod (140).

As a result, as shown in FIG. 7, the insertion brush (111), the tension brush (113), the holder member (112), and the separative rod (120), which are integrally connected to each other, are released from the outer cylinder member (130).

Figure 1:
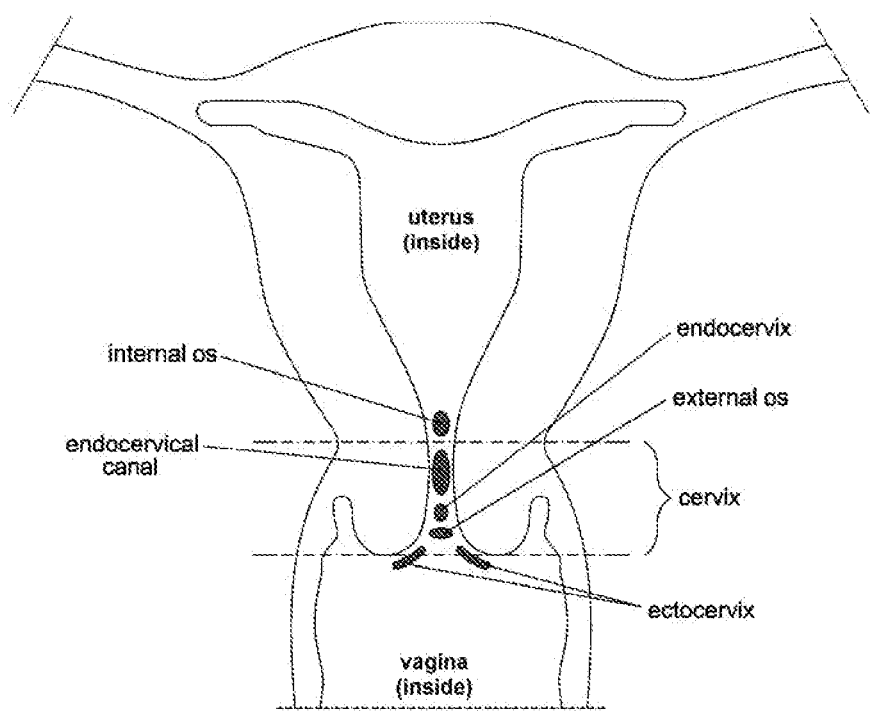
FIG. 1 is a simplified illustration of the periphery of uterus and cervix.
Figure 8:
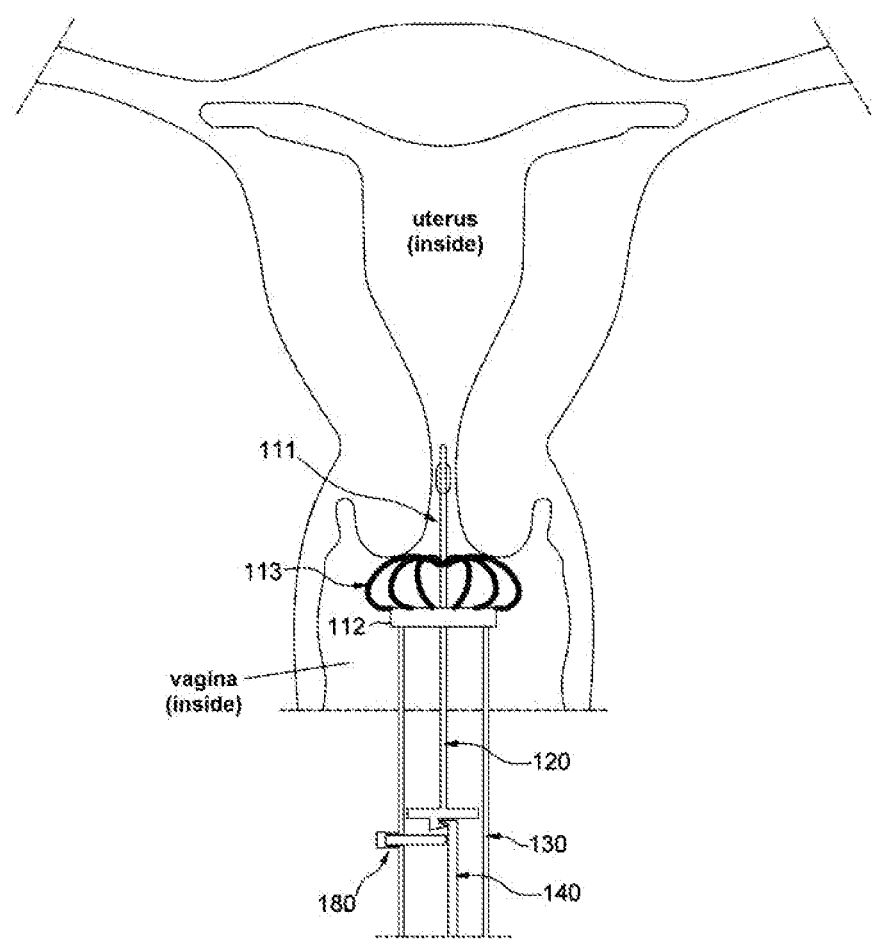
FIG. 8 is an exemplary view in which the exfoliative cell collection device of FIG. 2 is utilized for FIG. 1.

FIG. 8 is an exemplary view in which the exfoliative cell collection device of FIG. 2 is utilized for FIG. 1. Referring to FIGS. 1 and 8, when the tension brush (113) is laterally extended as shown in FIG. 8, it is configured that the tension brush (113) contacts relatively wide the ectocervix and that the insertion brush (111) is slightly inserted into the cervix.

In this case, the tension brush (113) and the insertion brush (111) were adjusted so as to be suitable for young women. The tension brush (113) may collect exfoliative cells relatively more at a portion of ectocervix. The insertion brush (111) may intensively collect exfoliative cells at portions of endocervix of cervix and external os.

Figure 9:
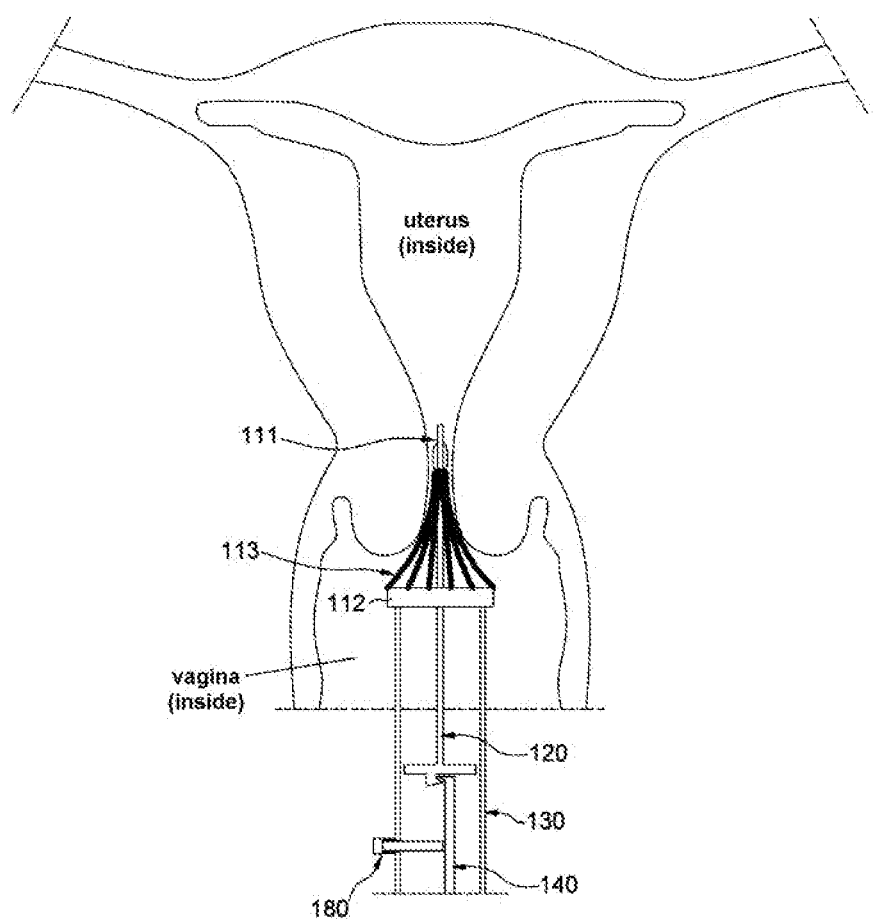
FIG. 9 is an exemplary view in which the exfoliative cell collection device of FIG. 4 is utilized for FIG. 1.

FIG. 9 is an exemplary view in which the exfoliative cell collection device of FIG. 4 is utilized for FIG. 1. Referring to FIGS. 1 and 9, when the tension brush (113) is longitudinally extended as shown in FIG. 9, it is configured that the tension brush (113) may be inserted more into the cervix toward the uterus so that the tension brush (113) may more effectively collect the exfoliative cells in the cervix than in FIG. 8.

At this time, the insertion brush (111) is configured so that its front end portion may penetrate the cervix and then reach the internal os in the entrance of the uterus.

In this case, the tension brush (113) and the insertion brush (111) were adjusted so as to be suitable for older women. The tension brush (113) may intensively collect exfoliative cells at the inner portion of cervix rather than at ectcervix. The insertion brush (111) may penetrate the cervix and then may collect exfoliative cells at a portion of internal os in the entrance of the uterus.

As described above, as the insertion brush (111) and the tension brush (113) are provided together, the user may simultaneously collect exfoliative cells at cervix as well as inner area of uterus by one operation.

Figure 10:
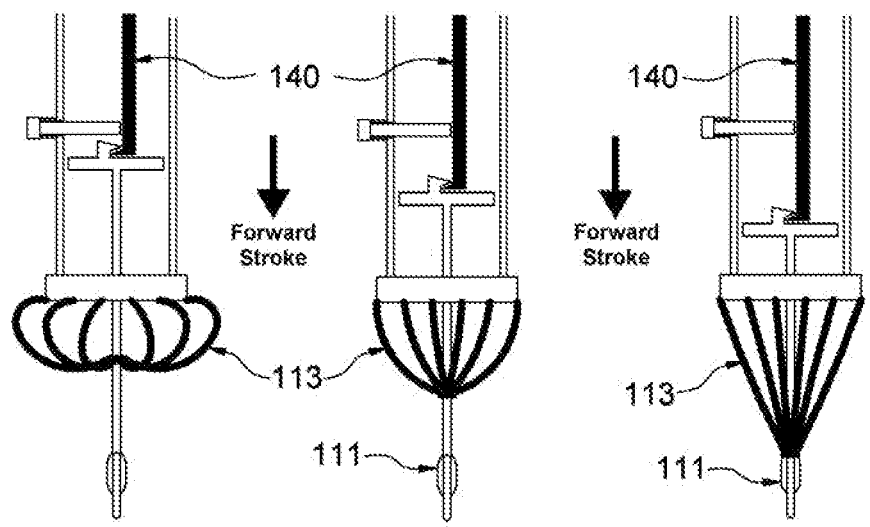
FIG. 10 is a view in which the shape of the tension brush is adjusted in the present invention.
Figure 11:
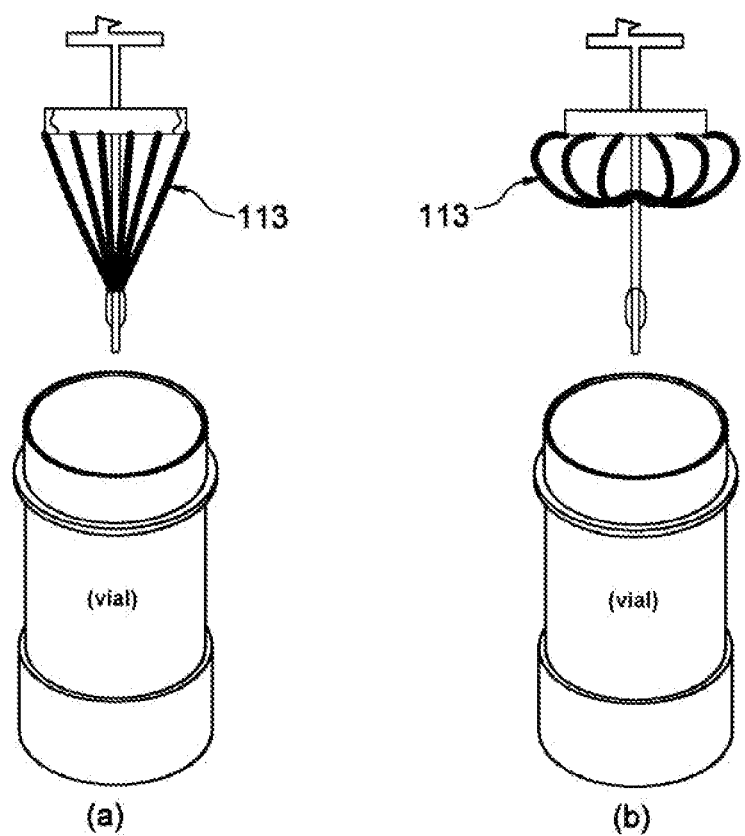
FIG. 11 is a view in which a front end portion is released and then put into a vial in the present invention.

FIG. 10 is a view in which the shape of the tension brush (113) is adjusted in the present invention. FIG. 11 is a view in which a front end portion (111, 113) is released from the exfoliative cell collection device of the present invention and then is put into a vial.

The technical solution of the present invention is to provide a device construction which is convenient for collecting exfoliative cells at various points of cervix. In order to achieve the uterus examination, exfoliative cells have to be collected at outside of cervix and inside of vagina. Because collection environment is completely different for these portions of body, in the conventional art, it is common to use separate collecting tools for each of portions, which are quite inconvenient. On the other hand, the present invention provides a device construction which enables a user to collect exfoliative cells at multiple portions with a single device.

For this purpose, the present invention is configured such that a user may adjust the shape of the exfoliative cell collecting part to be fat or sharp. Referring to FIG. 10, the tension brush (113) is fat when the movable rod (140) is positioned at the most rear. Further, as the tension brush (113) is pushed forward, the tension brush (113) becomes sharper.

First, a user may make the tension brush (113) be fat, and then let the tension brush (113) contact the outside of the cervix for collecting exfoliative cells at that portion. Subsequently, when the user intends to collect exfoliative cells inside of her body, the user may push the movable rod (140) forward so as to make the tension brush (113) be appropriately sharper, and then may push the device inside of her body.

Through the above-described operations, the front end portion, specifically, the insertion brush (111) and the tension brush (113) of the exfoliative cell collection device of the present invention are attached with the exfoliative cells which have been collected out of the user. Then, a procedure of releasing the portion to which exfoliative cells are attached from the main body of the collection device, and then of putting the released portion into a vial.

Meanwhile, the procedure of releasing the front end portion from the main body and then putting the release portion into a vial shall be carefully handled. The user should put the collected exfoliative cells into the vial without touching the cells so as to prevent the exfoliative cells from being contaminated. However, because vial inlet is very narrow in general, there is a risk of dropping the collected exfoliative cells on the floor. Considering the above, the present invention is configured such that the tension brush (113) becomes the most sharp when the front end portion is released from the main body.

Referring to FIG. 11, the tension brush (113) may be safely put into the vial if the tension brush (113) is sharp as shown in (a) when the front end portion of the exfoliative cell collection device is released from the main body. On the contrary, if the tension brush (113) is fat as shown in (b) when released from the main body, there is a risk that the tension brush (113) is caught on the vial inlet. Contamination may be caused by contact at the vial inlet. In some cases, the collected exfoliative cells may be completely spoiled due to splashing out of the vial. Accordingly, the present invention is configured such that the tension brush (113) becomes sharp when the front end portion is released from the main body.

However, when the exfoliative cell collection device of the present invention is inserted into user's body, the tension brush (113) becomes sharp. If a user is a little careless in collecting exfoliative cells inside her body, the front end portion may be released from the main body while the exfoliative cell collection device is still inside her body, which is very dangerous situation.

Accordingly, the present invention has been configured in order to ensure that users may safely use the exfoliative cell collection device without worrying about such a dangerous situation. In particular, the present invention has been configured such that, by the cooperation of the rod stopper (171) and the outer cylinder stopper (172), the backward pressing member (160) provides a backward elastic force to the movable rod (140), thereby making a force to allow the movable rod to continuously move backward. By this constitution, the releasing condition of the front end portion has been restricted. In order that the front end portion of the exfoliative cell collection device is stroked forward and then becomes released from the main body, user's explicit operation should be made. In addition, by restricting the releasing condition of the separative rod (120) and the push-releasing member (180) with mechanical latch, a little carelessness does not cause the front-end portion be released from the main body.

The invention claimed is:

1. An exfoliative cell collection device for uterus examination for collecting exfoliative cells at cervix and its surrounding area, comprising:
  an insertion brush (111) being inserted into a cervix;
  a separative rod (120) being connected to a rear end portion of the insertion brush, wherein the separative rod (120) is longitudinally stroked forward or backward along the insertion brush;
  an outer cylinder member (130) having a hollow cylindrical shape through which the rear end portion of the separative rod may go in and out, wherein the outer cylinder member (130) guides the forward and backward strokes of the separative rod;
  a holder member (112) being detachably connected to a front end portion of the outer cylinder member with surrounding the front end portion of the outer cylinder member;
  a plurality of tension brush (113) being mounted along a rim of the holder member, wherein one end of each tension brush is connected to the holder member and the other end of each tension brush is connected to the rear end portion of the insertion brush so as to be compatible with the shape of inside and outside of the cervix, wherein each tension brush provides gradual longitudinal extension by gradual unfolding in association with the forward stroke of the separative rod, and wherein each tension brush provides gradual lateral extension by gradual folding in association with the backward stroke of the separative rod;
  a movable rod (140) being detachably connected to the rear end portion of the separative rod while being inserted into the inner side of the outer cylinder member, wherein the movable rod (140) strokes the separative rod forward or backward when the movable rod (140) is longitudinally stroked forward or backward along the outer cylinder member;
  a pressing block (141) being connected to the rear end portion of the movable rod, wherein the pressing block (141) strokes the movable rod forward or backward when the pressing block (141) goes in and out of the outer cylinder member by user operation in the rear end portion of the outer cylinder member;
  a tension pressing member (150) being longitudinally connected to the side of the movable rod, wherein the tension pressing member (150) holds position of the movable rod by pressing the inner wall of the outer cylinder member so as to block a natural movement of the movable rod forward or backward;
  a rod stopper (171) protruding from the movable rod;
  an outer cylinder stopper (172) protruding inward from the inner wall of the outer cylinder member at a relatively forward position than the rod stopper;
  a backward pressing member (160) being disposed between the rod stopper (171) and the outer cylinder stopper (172) in the inner side of the outer cylinder member, wherein the backward pressing member (160) has a spring having one end contacting the rod stopper (171) and the other end contacting the outer cylinder stopper (172), and wherein the backward pressing member (160) provides the movable rod (140) with backward elastic force so that the movable rod (140) continuously has the force of backward moving as the spring presses the rod stopper (171) with respect to the outer cylinder stopper (172);
  a push-releasing member (180) pushing the front end portion of the movable rod from the inner wall of the outer cylinder member while being mounted on the outer cylinder member; and
  a tension hook member (190) being formed at the front end portion of the outer cylinder member, wherein the front end portion of the outer cylinder member is connected to the holder member, wherein the tension hook member (190) fits inside of the holder member in a hook shape by an elastic force when the tension hook member (190) slides into the holder member, and wherein the tension hook member (190) is released from the holder member by a series of forward strokes of the separative rod through the longitudinal extension of the tension brush by the forward stroke of the separative rod.

2. The exfoliative cell collection device for uterus examination of claim 1,
  wherein the movable rod (140) includes:
  a first latching hook (142) having a bended front end portion for providing a hook attachment and detachment;
  wherein the separative rod (120) includes:
  a second latching hook (121) having a bended rear end portion for providing a hook attachment and detachment with the first latching hook (142); and
  a guide rib (122) protruding around the rim of body portion thereof adjacent to the second latching hook, wherein the guide rib (122) contacts the inner wall of the outer cylinder member by the protrusion, and wherein the guide rib (122) guides the forward and backward strokes of the separative rod;
  wherein the push-releasing member (180) is mounted on the outer cylinder member to be adjacent to the first latching hook (142) in the maximum forward stroke of the movable rod (140), and
  wherein the push-releasing member (180) pushes the front end portion of the movable rod in response to user's push operation so as to let the first latching hook (142) be released from the second latching hook (121).

3. The exfoliative cell collection device for uterus examination of claim 2, wherein
  the outer cylinder member (130) includes:
  a plurality of latching holes (131) being longitudinally formed along the outer cylinder member adjacent to the tension pressing member, wherein the latching holes (131) penetrate the inside and outside of the outer cylinder member; and
  a latching slot (132) being formed in a slot shape longitudinally extending along the outer cylinder member, wherein the latching slot (132) is positioned on the holder member than the latching holes are; and
  wherein the tension pressing member (150) includes:
  a plurality of position adjusting protrusions (151) protruding to contact the inner wall of the outer cylinder member along the longitudinal direction of the tension pressing member, wherein the position adjusting protrusions (151) are positioned corresponding to the plurality of latching holes, wherein the position adjusting protrusions (151) are individually inserted into the plurality of latching holes by the elastic force of the tension pressing member, and wherein the position of the latching holes into which the position adjusting protrusions (151) are inserted changes by the forward or backward stroke of the movable rod; and a pressing protrusion (152) protruding along the longitudinal direction of the tension pressing member, wherein the pressing protrusion (152) is positioned on the holder member than the position adjusting protrusions are, wherein the pressing protrusion (152) is inserted into the latching slot by the elastic force of the tension pressing member, wherein the pressing protrusion (152) protrudes more than the position adjusting protrusions so that a user's push operation while the pressing protrusion (152) is inserted into the latching slot enables the position change between the latching holes and the position adjusting protrusions.

\* \* \* \* \*